US008470982B2

(12) United States Patent
Knochel et al.

(10) Patent No.: US 8,470,982 B2
(45) Date of Patent: Jun. 25, 2013

(54) SOLUTIONS OF ANHYDROUS LANTHANIDE SALTS AND ITS PREPARATION

(75) Inventors: Paul Knochel, München (DE); Arkady Krasovskiy, La Jolla, CA (US); Felix Kopp, New York, NY (US)

(73) Assignee: Ludwig-Maximilians-Universitaet, Munich (DE)

( * ) Notice: Subject to any disclaimer, the term of this patent is extended or adjusted under 35 U.S.C. 154(b) by 574 days.

(21) Appl. No.: 11/991,131

(22) PCT Filed: Sep. 1, 2006

(86) PCT No.: PCT/EP2006/065912
§ 371 (c)(1),
(2), (4) Date: Apr. 2, 2009

(87) PCT Pub. No.: WO2007/026014
PCT Pub. Date: Mar. 8, 2007

(65) Prior Publication Data
US 2009/0326235 A1 Dec. 31, 2009

(30) Foreign Application Priority Data
Sep. 1, 2005 (EP) .................................... 05019026

(51) Int. Cl.
*C07F 5/00* (2006.01)
(52) U.S. Cl.
USPC .......................................................... 534/15
(58) Field of Classification Search
None
See application file for complete search history.

(56) References Cited

U.S. PATENT DOCUMENTS

| | | | |
|---|---|---|---|
| 4,835,398 A | 5/1989 | Nakamura et al. | |
| 5,336,653 A * | 8/1994 | Shibasaki et al. | 502/170 |
| 2002/0151626 A1 | 10/2002 | Isaka | |
| 2005/0137425 A1 | 6/2005 | Abramson et al. | |

FOREIGN PATENT DOCUMENTS

EP  1 153 657  11/2001

OTHER PUBLICATIONS

LeBrun, A New Preparation of Lanthanide Alkoxides, and some Applications in Catalysis, Tetrahedron Letters, 32(21), 2355-2358.*
Database WPI, Section Ch, Week 198407, Derwent Publications Ltd., London, GB, Class C03, AN 1984-039618, XP002371251 & JP 59 001432 A (Shinetsu Chem Ind Co Ltd) (Jan. 6, 1984) Abstract.
Database WPI, Section Ch, Week 199108, Derwent Publications Ltd., London, GB; Class E33, an 1991-056103, XP002371250 & SU 1 551 653 A (As USSR Fare Chem), (Mar. 23, 1990) Abstract.
Gong et al, "Thermodynamic assessment of LiCl-NdCl3 and LiCl-PrCl3 quasi-binary systems," Journal of Alloys and Compounds, Elsevier Sequoia, Lausanne, CH, vol. 396, No. 1-2, pp. 92-99 (Jun. 21, 2005) XP004905087, ISSN: 0925-8388.

Kabayashi et al., "Rare-earth metal triflates in organic synthesis," Chemical Reviews, vol. 102, No. 6, pp. 2227-2302 (Dec. 6, 2002) XP002415199.
Novikov et al., "1-Bromo-1-lithioethene: A practical reagent for the efficient preparation of 2-Bromo-1-alken-3-ols," Organic Letters, vol. 5, No. 13, pp. 2263-2266 (2003) XP002371241.
International Search Report for International Application No. PCT/EP2006/065912 dated Jan. 30, 2007.
Notification Concerning Transmittal of International Preliminary Report on Patentability for International Application No. PCT/EP2006/065912 dated Mar. 13, 2008.
Dimitrov, V., et al., "Anhydrous cerium(III) chloride—effect of the drying process on activity and effciency," Tetrahedron Lett., 37, 6787-6790 (1996).
Eckenberg, P., et al., "Addition of cerium reagents derived from (trimethylsilyl)propargyl bromide to aldehydes," Liebigs Ann. Chem., 673-677 (1994).
Edelmann, F.T., et al., "Synthesis and structural chemistry of non-cyclopentadienyl organolanthanide complexes," Chem. Rev., 102, 1851-1896 (2002).
Fisher, S., et al., "Cerium(III)—catalyzed addition of diethylzinc to carbonyl compounds," Synlett., 1922-1924 (2002).
Fukazawa, S., et al., "1,2-Regioselective reduction of α,β-unsaturated carbonyl compounds with lithium aluminum hydride in the presence of lanthanoid salts," J. Chem. Soc. Perkin Trans. I, 1929-1932 (1986).
Gemal, A.L., et al., "Lanthanoids in organic chemistry. 6. The reduction of α-enones by sodium borohydride in the presence of lanthanoid chlorides: synthetic and mechanistic aspects," J. Am. Chem. Soc., 103, 5454-5459 (1981).
Groth, U., et al., "Diastereoselective Ce(O$i$Pr)$_3$-catalyzed pinacol couplings of aldehydes," Angew.Chem. Int. Ed., 39, 574-576 (2000).
Groth, U., et al., "Diastereoselective Ce(III)-catalyzed pinacol couplings of aldehydes," Synlett., 129-131 (2001).
Hatano, M., et al., "Highly alkyl-selective addition to ketones with magnesium ate complexes derived from Grignard reagents," Org. Lett., 7, 573-576 (2005).
Imamoto, T., et al., "Organocerium reagents. Nucleophilic addition to easily enolizable ketones," Tetrahedrom Lett., 4233-4236 (1984).
Imamoto, T., et al., "Cerium chloride-promoted nucleophilic addition of Grignard reagents to ketones. An efficient method for the synthesis of tertiary alcohols," Tetrahedron Lett., 26, 4763-4766 (1985).

(Continued)

*Primary Examiner* — Paul Dickinson
(74) *Attorney, Agent, or Firm* — Jenkins, Wilson, Taylor & Hunt, P.A.

(57) ABSTRACT

The present invention relates to anhydrous solutions of $MX_{3-z}LiA$ in a solvent, wherein M is a lanthanide including lanthanum, or yttrium or indium; z>0; and X and A are independently or both monovalent anions, preferably Cl, Br or I. The solution is readily prepared by dissolving or suspending $MX_3$ or its hydrate and z equiv LiA in water or hydrophilic solvents, or mixtures thereof, removing the solvent under vacuum and dissolving the resulting powder in another solvent. The solution of $MX_{3-z}LiA$ can advantageously be used e.g. in addition reactions of Grignard reagents to ketones and imines. Even the catalytic use of $MX_{3-z}LiA$ is possible.

30 Claims, No Drawings

OTHER PUBLICATIONS

Imamoto, T., et al., "Reactions of carbonyl compounds with Grignard reagents in the presence of cerium chloride," J. Am. Chem. Soc., 111, 4392-4398 (1989).

Kobayashi, S., et al., "Development of novel Lewis acid catalysts for selective organic reactions in aqueous media," Acc. Chem. Res., 35, 209-217 (2002).

Krasovskiy, A., "A LiCl-mediated Br/Mg exchange reaction for the preparation of functionalized aryl- and heteroarylmagnesium compounds from organic bromides," Angew. Chem. Int. Ed., 43, 3333-3336 (2004).

Li, W.-D. Z., et al., "A novel synthesis of functionalized allylsilanes," Org. Lett., 6, 1849-1852 (2004).

Luche, J.-L., J. "Lanthanides in organic chemistry. 1. Selective 1,2 reductions of conjugated ketones," J. Am. Chem. Soc., 100, 2226-2227 (1978).

Schumann, H., et al., "Lewis-acidic organometallic compounds of the lanthanides and the alkaline earth metals as catalysts for the activation of carbonyl groups," Pure and Appl. Chem., 73, 279-282 (2001).

Shenglof, M., et al., "Lanthanide assisted cross-couplings of aryl bromides with triethylaluminum," Tetrahedron Lett., 44, 8593-8595 (2003).

Tsvelikhovsky, D., et al., "Lanthanide-promoted ethylation of Schiff bases by triethylaluminum" Org. Lett., 6, 1995-1997 (2004).

* cited by examiner

SOLUTIONS OF ANHYDROUS LANTHANIDE SALTS AND ITS PREPARATION

The present application relates to anhydrous solutions of lanthanide salts, its preparation and its use.

Lanthanide(III) salts have been intensively used to activate carbonyl compounds or imine derivatives towards the 1,2-addition of organometallics.[1a] The oxophilic nature of lanthanide salts favors the 1,2-addition reaction comparatively to competitive reactions such as enolization or reduction (by β-hydride transfer).[2a] The 1,2-addition of complex hydrides to carbonyl functions can also be promoted and the presence of lanthanide salts can dramatically reduce competitive reduction e.g. of double bonds.[2d,e] Further applications were published on the field of lewis acid catalyzed cycloaddition reactions.[1b] The activity of the catalyst strongly depends on its drying[3] and especially on its solubility.[4] Only few lanthanide salts are soluble in appreciable amounts in organic solvents.[5]

So far, the Imamoto method (using $CeCl_3$) was used to promote the addition of organometallic compounds to carbonyl compounds or imine derivatives. However, this method fails in the case of the addition of functionalized Grignard reagents to carbonyl derivatives.

Usually, lanthanide halides are heated under vacuum to remove the water. This procedure often leads to insoluble, polymeric lanthanide halides, or the water can not be removed entirely. In general, the lanthanide salts tend to form a polymeric structure. This polymeric lanthanide salt is insoluble, or at least very poorly soluble.

Thus, it would be desirable to be able to easily prepare anhydrous solutions of these salts. Furthermore, it would be desirable to obtain a solution of lanthanide halides with improved activity in 1,2-addition reactions of organometallics to carbonyl compounds or imine derivatives. The use of $MX_3$ in the reaction of Grignard reagents with enolizable or sterically hindered carbonyl compounds as well as imines would additionally be beneficial.

Solutions to these problems are given by the subject matter of the independent claims. Preferred embodiments are set forth in the dependent claims.

SUMMARY OF THE INVENTION

The inventors have found that the use of lithium salts, LiA, preferably LiCl, is beneficial for the preparation of anhydrous solutions of metal salts ($MX_3$, M=Ln, Y, In).

An anhydrous complex salt of those metals can readily be prepared from $MX_3$ in the presence of lithium salts. This anhydrous salt can be dissolved in e.g. ethereal solvents like THF. This applies to all lanthanide elements including lanthanum as well as to yttrium and indium.

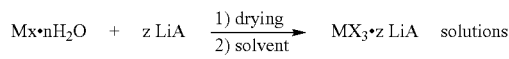

According to a first aspect of the invention, an anhydrous solution of $MX_3 \cdot z$ LiA in a solvent is provided, wherein M is yttrium, indium or a lanthanide including lanthanum; z>0; and X and A are independently or both monovalent anions.

According to a second aspect of the invention, an anhydrous solution of $MX_3 \cdot z$ LiA in a solvent is prepared by a method comprising the following steps:

a) Close mixing of $MX_3$ and z equivalents LiA, optionally in a first solvent;
b) Removing the solvent and/or water from the mixture formed in step a);
c) Adding a second solvent to the powder formed in step b) to form a solution;
wherein M, X, A and z are defined as above.

According to a third aspect of the invention, an anhydrous salt of $MX_3 \cdot z$ LiA is provided, wherein M, X, A and z are defined as above.

According to a fourth aspect of the invention, the use of a solution of $MX_3 \cdot z$ LiA in a chemical reaction is provided.

According to a preferred embodiment, X and A are independently or both selected from the group consisting of F; Cl; Br; I; CN; SCN; NCO; $HalO_n$, wherein n=3 or 4 and Hal is selected from Cl, Br and I; $NO_3$; $BF_4$; $PF_6$; $AsF_6$; $SbF_6$; H; a carboxylate of the general formula $RCO_2$; a disilazide of the general formula $(R_3Si)_2N$; a thiolate of the general formula SR; $RP(O)O_2$; SCOR; an amine of the general formula RNH; a dialkyl or diarylamine of the general formula $R_2N$, wherein R is defined as below or $R_2N$ represents a cyclic alkylamine; a phosphine of the general formula $PR_2$, wherein R is defined as below or $PR_2$ represents a cyclic phosphine; $O_nSR$, wherein n=2 or 3; or $NO_n$, wherein n=2 or 3; and derivatives thereof;

wherein R is a substituted or unsubstituted $C_4$-$C_{24}$ aryl or a $C_3$-$C_{24}$ heteroaryl, containing one or more heteroatoms as B, O, N, S, Se, P, or Si; a linear or branched, substituted or unsubstituted $C_1$-$C_{20}$ alkyl; a $C_2$-$C_{20}$ alkenyl or a $C_2$-$C_{20}$ alkinyl; or a substituted or unsubstituted $C_3$-$C_{20}$ cycloalkyl; or derivatives thereof, or H.

Preferably, X and A are the same anions, most preferably Cl.

According to another preferred embodiment, $z \geq 1$. A further preferred value for z is $z \geq 2$, since presumably a stable complex anion is formed. z is the molar amount of LiA compared to the molar amount of M. Nevertheless, even traces of LiA can promote the solution of $MX_3$ in a solvent. Thus, any ratio of LiA is possible according to the invention. LiA can even be added to a commercially available anhydrous salt of $MX_3$ to ease the solution of the anhydrous salt in a solvent. In view of the above, in further preferred embodiment, z is in the range of 0.5<z<3, preferably in the range of $2 \leq z < 3$.

The present invention applies to metal salts. The group of the lanthanides comprises most of these metals. The term metal and lanthanide are thus used interchangeable within this application. M may be selected from yttrium or indium or the lanthanides including lanthanum, i.e. lanthanum, cerium, praseodymium, neodymium, promethium, samarium, europium, gadolinium, terbium, dysprosium, holmium, erbium, thulium, ytterbium, lutetium. Especially preferred lanthanides are lanthanum (La), cerium (Ce), praseodymium (Pr) and neodymium (Nd).

Even though the invention is described above for the use of monovalent anions leading to a stoichiometric formula of $MX_3$, the use of di- or tri- or multivalent anions is possible. Accordingly, e.g. sulfate or phosphate can be used as anions, resulting in salts like $M_2(SO_4)_3$ or $MPO_4$.

The present invention is applicable to a solution of $MX_3 \cdot z$ LiA in a solvent which is capable of dissolving $MX_3 \cdot z$ LiA. Preferred solvents are selected from cyclic, linear or branched mono or poly ethers, thioethers, amines, phosphines, and derivatives thereof containing one or more additional heteroatoms selected from O, N, S and P, preferably tetrahydrofuran (THF), 2-methyltetrahydrofuran, dibutyl ether, diethyl ether, tert-butylmethyl ether, dimethoxyethane, dioxanes, preferably 1,4-dioxane, triethylamine, ethyldiisopropylamine, dimethylsulfide, dibutylsulfide; cyclic amides, preferably N-methyl-2-pyrrolidone (NMP), N-ethyl-2-pyrrolidone (NEP), N-butyl-2-pyrrolidone (NBP); cyclic, linear or branched alkanes and/or alkenes wherein one or more hydrogens are replaced by a halogen, preferably dichloromethane, 1,2-dichloroethane, $CCl_4$; urea derivatives, preferably N,N'-dimethylpropyleneurea (DMPU); aromatic, heteroaromatic or aliphatic hydrocarbons, preferably benzene, toluene, xylene, pyridine, pentane, cyclohexane, hexane, heptane; hexamethylphosphorus triamide (HMPA), $CS_2$; or combinations thereof.

However, a person skilled in the art will be able to determine a solvent without undue burden and without inventive activity by simple solution experiments of the anhydrous salt.

According to yet another preferred embodiment of the invention, the solution according to the invention contains M in a concentration of up to 3 mol/l, including 1 mol/l. Preferably, the solution contains M in a concentration of 0.05-2 mol/l, more preferably in a concentration of 0.1-1-5 mol/l, even more preferably in a concentration of 0.2-1.3 mol/l and most preferably in a concentration of 0.3-0.8 mol/l. Concentrations of 0.1 mol/l, 0.2 mol/l, 0.25 mol/l, 0.33 mol/l, 0.5 mol/l, 1.0 mol/l and 2.0 mol/l are especially preferred. Nevertheless, solution may also be prepared in a concentration in the mmol range.

The solution can be stored for months without loss of activity of the lanthanides under an inert gas atmosphere, preferably an anhydrous inert gas atmosphere. Furthermore, drying agents may be added to the solution. Any drying agent, which is insoluble in the solvent, may be used. Examples for such drying agents include, but are not limited to molecular sieves, sodium hydride, calcium hydride, silica perls, silica powder, aluminium oxide, sodium sulfate, magnesium sulfate and sodium phosphate.

The term anhydrous as used herein relates to a salt or solution of reduced water content. These solutions are also known as non-aqueous solutions. Preferably, the water content in relation to the content of M is as low as possible. The remaining water content may disturb e.g. the addition reaction of a Grignard reagent to a ketone. It is thus preferred to reduce the water content to a minimum. However, if the solution still contains remaining water, the use of the solution according to the invention may nevertheless be beneficial to a reaction, but an excess of reactants may be necessary. In general, the less water is contained in the solution, the less metal organic reagent is needed for a completion of the reaction. The inventive concept primarily permits the preparation of anhydrous solutions of $MX_3$ in a solvent by means of the addition of LiA. The addition of LiA increases the solubility of the lanthanide salt and allows an easier removal of remaining water.

A general procedure for the preparation of solutions of $MX_3$.z LiA involves the close mixing of $MX_3$ and z equivalents LiA. The mixing may include the mixing of the solids of $MX_3$ and LiA or the mixing of the corresponding hydrates or solvent aducts. The mixing may also be carried out in form of a solution or a suspension in water or in a hydrophilic solvent or a mixture thereof. Hydrophilic solvents may include alcohols, ketones and ethers, or mixtures thereof. The mixture may also be in the form of a slurry or a dispersion. However, if the solids are mixed, the admixture should be performed by means of mechanical stirring in order to ensure an intimate mixture. Also, if the mixture is in the form of a solution, slurry or dispersion, the mixing may comprise stirring. The mixing of the components should preferably be intense to allow an exchange of reactants and ions. This exchange of reactants or ions is promoted in a solvent, but is not restricted thereto.

From the resulting mixture, any solvent and/or the water is removed. This may be achieved by the application of reduced pressure. The reduced pressure may even be a high vacuum with a pressure of as low as 0.01 mmHg. The removal of any solvent and/or water may be carried out under stirring like mechanical stirring. In another preferred embodiment, any solvent and/or water is removed by freeze drying.

The mixture may also be heated to accelerate the removal. To further dry the mixture, it may be heated up to 160° C., or even up to 200° C., preferably under reduced pressure. In a preferred embodiment, the mixture is stirred during the heating and in still another preferred embodiment, the heating is carried out stepwise while keeping the temperature at different levels for up to several hours. By way of an example, the mixture may be heated to 40° C. for 4 hours, to 60° C. for 4 hours, to 80° C. for 4 hours, to 100° C. for 4 hours, to 120° C. for 4 hours, to 140° C. for 4 hours, to 160° C. for 4 hours. This procedure of a slowly continuous and/or stepwise rise of the temperature avoids the formation of polymeric products, which are difficult to dissolve in a solvent and also completely inactive in the desired reaction. It is also important to note that the solids have to be crushed during the intervals of heating or by mechanical stirring continuously in order to avoid a formation of polymers.

The resulting powder may be stored under an inert gas atmosphere until use. Preferably after cooling the resulting powder to room temperature, a solvent may be added to prepare a solution of $MX_3$.z LiA. Additionally, drying agents may be added before or after the addition of a solvent. The drying agent is preferably insoluble in the selected solvent. The drying agent is preferably selected from the group of molecular sieves, sodium hydride, calcium hydride, silica perls, silica powder, aluminium oxide and sodium phosphate but not restricted thereto. The drying agent may be removed prior to use.

The solvent may be selected from any solvent or mixture of solvents capable of dissolving $MX_3$.z LiA. Preferred solvents are defined as above.

The resulting solution has a water content of less than 15% compared to the content of M, preferably less than 10%, preferably even less than 5% and most preferred less than 1%.

The solvent may be added in an amount such that the resulting solution has a defined concentration. Preferred concentrations are e.g. 0.1 M solution, 0.2 M solution, 0.25 M solution, 0.33 M solution, 0.5 M solution or 1.0 M solution. Nevertheless, a person skilled in the art will recognize, that any concentration up to the maximum concentration of the solid, i.e. the solubility product is reached, can easily be prepared. This resulting solution may be stored without loss of activity under an inert gas like e.g. nitrogen or noble gases like argon, or by the addition of a drying agent, as mentioned above.

In a preferred embodiment, the remaining amount of water in the solution may be further reduced by the addition of molecular sieves or other drying agents. The dried molecular sieves further bind water from the solution. It is also possible to store the solution over molecular sieves. Preferred molecular sieves are molecular sieves of 4 Å. The molecular sieves may be removed prior to use e.g. by filtration.

In another preferred embodiment of the invention, the remaining amount of water may be further reduced by a joint removal of the solvent and the remaining water, e.g. an azeotropic distillation of THF as solvent, or by additional drying using e.g. $SOCl_2$. The resulting powder may be re-dissolved in any solvent mentioned above capable of dissolving $MX_3$.z LiA. The solvent may also be removed prior to shipping to reduce the shipping cost. A solution may easily be restored prior to use. The resulting solid or powder will contain $MX_3 \cdot z$ LiA. It may further contain remaining solvent in the form of an adduct of the solvent to the salt. The remaining solvent will ease the re-solution of the salt in a solvent.

The solution according to the invention is beneficial to many areas of chemistry. By way of example, these favorable properties are given for selected types of reactions. However, a person skilled in the art will appreciate that these solution may be used in many other fields, where lanthanides are used. The following examples are thus not to be understood as limiting the scope of the invention.

The resulting solution is favorably applicable to promote the reaction of carbonyl derivatives or carboxylic acid derivatives with nucleophiles like Grignard reagents, lithiumorganic reagents or complex hydrides. This solution especially promotes the addition of Grignard reagents (1) to various types of hindered and easily enolizable ketones (2) leading to tertiary alcohols of type 3, as illustrated in Scheme 1 below.

Scheme 1. Products of the reaction of organomagnesium reagents with ketones, wherein $R^1$, $R^2$ and $R^3$ are independently substituted or unsubstituted $C_4$-$C_{24}$ aryl or $C_3$-$C_{24}$ heteroaryl, containing one or more heteroatoms as B, O, N, S, Se, P, Si; linear or branched, substituted or unsubstituted $C_1$-$C_{20}$ alkyl, $C_2$-$C_{20}$ alkenyl or $C_2$-$C_{20}$ alkinyl; or substituted or unsubstituted $C_3$-$C_{20}$ cycloalkyl; or derivatives thereof;

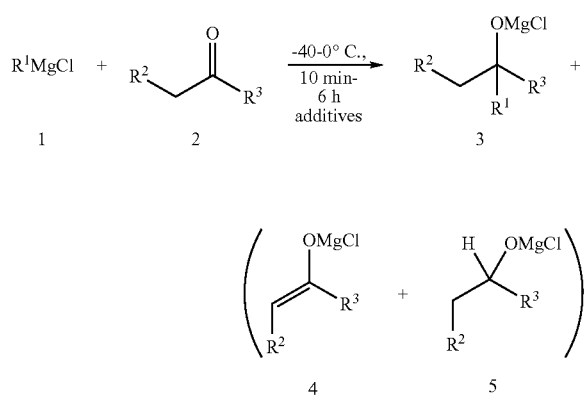

The side products usually obtained in these reactions are the enolization of the ketone leading to the corresponding magnesium enolate 4 and the β-hydride reduction leading to the alcohol 5. The addition of lanthanide salts minimizes these side reactions. The results of comparative examples are shown in Table 1 below.

As can be seen from Table 1 below, the reaction of hindered Grignard reagents or hindered ketones (e.g. compounds 1g, 1h and 2h in Table 1) is significantly improved. Furthermore, the addition to camphor (2j) is highly diastereoselective.

In the case of α,β-unsaturated ketones such as cyclohexenone, the addition of secondary alkylmagnesium compounds such as cyclopentylmagnesium chloride proceeds exclusively in the presence of $MX_3 \cdot z$ LiA, preferably $LaCl_3 \cdot 2LiCl$ leading to the desired tertiary allylic alcohol 6 in 93% yield. In the absence of such a salt, the only product observed is the allylic alcohol 7 which can be isolated in 77% yield (Scheme 2).

Scheme 2. 1,2-Addition of a Grignard reagent to cyclohexenone, promoted by $MCl_3 \cdot 2LiCl$ (where M is La).

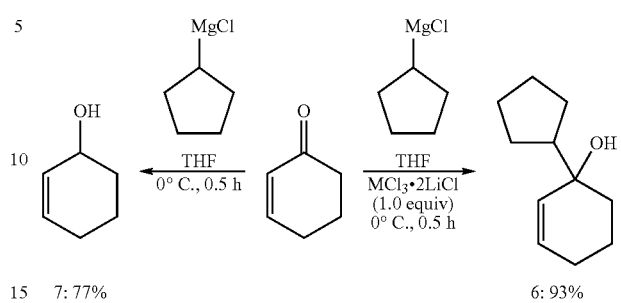

7: 77%  6: 93%

Metal(III) salts also promote the addition of organolithium compounds to carbonyl derivatives, explicitly shown for ketones in Scheme 3. Practically quantitative yields of desired alcohols can be achieved, whereas other methods showed worse results. Thus, addition of n-BuLi to cyclopentanone leads at 0° C. to the desired alcohol in 96-98% yield, whereas using Imamoto's procedure low temperatures (−78° C.) as well as longer reaction times are needed and the yields are lower.

Scheme 3. Addition of n-BuLi to cyclpentanone, promoted by $MCl_3 \cdot 2LiCl$ (where M is La).

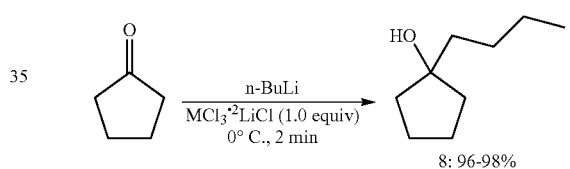

8: 96-98%

Imamoto (method A): -78° C., 3h, 77% (from BuLi)
Imamoto (method B): 0° C., 5h, 60% (from BuMgCl)

Finally, catalytic amounts of $MX_3 \cdot z$ LiA (e.g. 10 mol %) are sufficient to promote the addition of Grignard reagents to non-activated imines such as 9. Without the presence of the catalyst, the amine 10 is isolated in 15% yield, whereas in the presence of $LaCl_3 \cdot 2LiCl$ (10 mol %) the addition product 10 is obtained in 84% yield. Similarly, the addition of vinylmagnesium chloride to the imine 11 provides the bis-allylic amine 11 in 87% yield (Scheme 4). The catalytic use of lanthanide halides becomes possible with the use of the lanthanide solutions according to the invention.

Scheme 4. $LaCl_3 \cdot 2LiCl$-catalyzed addition of Grignard reagents to imines.

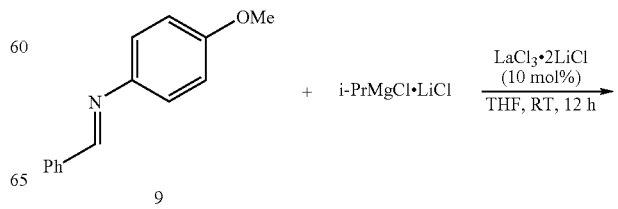

9

-continued

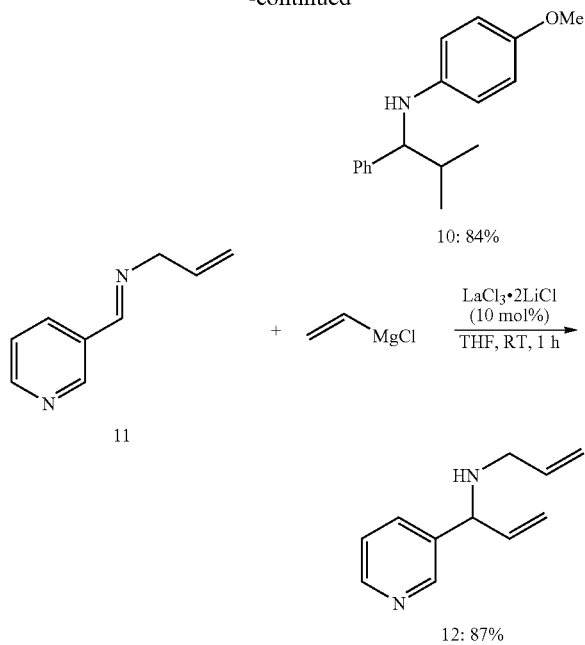

10: 84%

11 + MgCl → LaCl₃·2LiCl (10 mol%) / THF, RT, 1 h →

12: 87%

During the addition reaction of ketones or imines with Grignard reagents in the presence of $MX_3 \cdot z$ LiA, the solvents used are anhydrous solvents. The lanthanide salt can be recovered by different methodologies. For example, the addition of a trace of water initiates a precipitation of the lanthanide salt which can be easily removed from the reaction mixture. The precipitated salt can be used for recycling.

EXAMPLES

Example 1

Preparation of a Solution of $LaCl_3 \cdot 2LiCl$ in THF

In a round bottom flask commercially available $LaCl_3 \cdot 6H_2O$ (0.10 Mol, 35.3 g) was mixed with LiCl (0.20 Mol, 8.40 g) and water (100 mL) was slowly added with vigorous stirring. The resulting slurry was stirred in high vacuum (0.01 mm Hg) at RT for 4 h. Stirring was continued 4 h at 40° C., 4 h at 60° C., 4 h at 80° C., 4 h at 100° C., 4 h at 120° C., 4 h at 140° C. and finally 4 h at 160° C. The slow increase of temperature and highly efficient stirring are essential. The resulting solid was cooled to room temperature and THF was added until a total volume of 333 mL was reached. Then, molecular sieves (4 Å) were added and the resulting mixture was stirred vigorously for 1d at RT. Finally, all unsoluble material (mostly crushed molecular sieves) was filtered over a combined filter system (fresh molecular sieves/paper) under an argon atmosphere. By this procedure, a clear and colorless solution of $LaCl_3 \cdot 2LiCl$ was obtained that was stored until use at RT under argon.

Solutions of $YCl_3 \cdot 2LiCl$, $CeCl_3 \cdot 2LiCl$, $NdCl_3 \cdot 2LiCl$, $PrCl_3 \cdot 2LiCl$, $DyCl_3 \cdot 2LiCl$ and $ErCl_3 \cdot 2LiCl$ were also successfully prepared according Example 1.

Table 1 below gives an overview of different salts according to the invention and their solubility in THF. The salts were prepared from the corresponding lanthanide hydrates according to Example 1 (Method A) by replacing $LaCl_3 \cdot 6H_2O$ with the corresponding lanthanide hydrate and replacing LiCl by the corresponding lithium salt, where appropriate, or alternatively by combining the anhydrous salts under a nitrogen atmosphere (glovebox) and dissolving the resulting mixture in anhydrous THF (Method B). In some cases, heating (4 h, 50° C.) was applied. An aliquot of each of the 26 solutions was analysed by EDTA titration on the molarity of the solution.

TABLE 1

Results of the lanthanide solubility screening.

| entry | lanthanide source | lithium salt (equiv[1]) | method | molarity[2] |
|---|---|---|---|---|
| 1 | $LaCl_3$ | LiCl (2) | A | 0.40[3] |
| 2 | $LaCl_3$ | LiBr (2) | A[4] | 1.11 |
| 3 | $LaCl_3$ | LiI (3) | A[4] | 0.08 |
| 4 | $LaCl_3$ | LiOtBu (3) | A[4] | <0.01 |
| 5 | $LaCl_3$ | LiOtBu (3) | B | <0.01 |
| 6 | $LaCl_3$ | LiBr (3) | B[4] | 0.9 |
| 7 | $LaCl_3$ | $LiBF_4$ (3) | B[4] | 0.03[5] |
| 8 | $LaCl_3$ | $LiPF_6$ (3) | B[4] | 0.02 |
| 9 | $LaCl_3$ | LiOTf (3) | B[4] | 0.05 |
| 10 | $LaCl_3$ | LiH (3) | B[4] | 0.02 |
| 11 | $LaCl_3$ | $LiBH_4$ (3) | B[4] | 0.03 |
| 12 | $LaCl_3$ | $LiNH_2$ (3) | B[4] | 0.03 |
| 13 | $LaCl_3$ | LiOAc (3) | B[4] | 0.07 |
| 14 | $LaCl_3$ | Li(acac) (1) | B[4] | 0.04[5] |
| 15 | $LaCl_3$ | Li(acac) (2) | B[4] | 0.04[5] |
| 16 | $LaBr_3$ | LiBr (3) | B | 0.50 |
| 17 | $LaBr_3$ | LiCl (2) | B[4] | 0.60 |
| 18 | $LaBr_3$ | LiCl (3) | B[4] | 1.09 |
| 19 | $La(OTf)_3$ | LiCl (3) | B[4] | 0.02 |
| 20 | $La(OTf)_3$ | LiBr (3) | B[4] | 0.53 |
| 21 | $La_2(SO_4)_3$ | LiCl (3) | B[4] | 0.02 |
| 23 | $La_2(SO_4)_3$ | LiBr (3) | B[4] | 0.11[5] |
| 24 | $SmCl_3$ | LiCl (1) | B | 0.14 |
| 25 | $SmBr_3$ | LiCl (3) | B[4] | 0.67 |
| 26 | $SmBr_3$ | LiBr (3) | B[4] | 0.77 |

[1]Stoichiometry used for the preparation.
[2]Value represents the minimally achievable solubility; higher concentrations may be possible. Concentration determined by EDTA-Titration of an aliquot in a urotropine-buffered solution using methylthymol blue as indicator.
[3]Value obtained from industry collaboration.
[4]Heating to 50° C. for 4 h applied.
[5]±0.02; No sharp change of colour in EDTA titration.

Example 2

General Procedure for the Reactions with Ketones and Imines (A)

In a flame dried, argon-flushed Schlenk tube equipped with a septum and a magnetic stirring bar was placed $LaCl_3 \cdot 2LiCl$ in THF (0.33 M; 6.06 mL, 2.00 mmol, 1.00 equiv; In the case of imines, only 10 mol-% of $LaCl_3 \cdot 2LiCl$ in THF were used the missing volume was filled up with absolute THF). The ketone (2.00 mmol) was added neat and the resulting mixture was stirred for 1 h at RT. The reaction mixture was cooled to 0° C. and the Grignard reagent (solution in THF, 2.10 mmol, 1.05 equiv.) was added dropwise and the reaction mixture was allowed to stir at the same temperature. The reaction conversion was monitored by GC-analysis of reaction aliquots. After a complete conversion was reached, sat. aq. $NH_4Cl$ (2 mL) and water (2 mL) was added. The aqueous layer was extracted with ether (4×10 mL), the combined extracts were dried ($Na_2SO_4$) and evaporated in vacuo. The crude residue was purified by flash column chromatography.

Example 3

General Procedure for the Reactions with Ketones (B)

In a flame dried, argon-flushed Schlenk tube equipped with a septum and a magnetic stirring bar was placed $LaCl_3 \cdot 2LiCl$ in THF (0.33 M; 6.06 mL, 2.00 mmol, 1.00 equiv) at 0° C. Then, the Grignard reagent (solution in THF, 2.10 mmol, 1.05 equiv.) was added dropwise and the mixture was allowed to stir at the same temperature for 1 h. The ketone (2.00 mmol) was then added neat and the resulting mixture was allowed to warm up to 25° C. and stirred for 1 h at this temperature. The reaction conversion was monitored by GC-analysis of reaction aliquots. After a complete conversion was reached, sat. aq. NH$_4$Cl (2 mL) and water (2 mL) was added.

The aqueous layer was extracted with ether (4×10 mL), the combined extracts were dried (Na$_2$SO$_4$) and evaporated in vacuo and the crude residue was purified by flash column chromatography.

TABLE 1

Comparative reactions of ketones 2 with Grignard reagents 1 without additives and in the presence of CeCl$_3$ or MCl$_3$·2LiCl.

| Entry | Grignard reagent 1 | Ketone of type 2 | Product of type 3 | Without additives (%)[a] | CeCl$_3$ (%)[b] | MCl$_3$·2LiCl (%) |
|---|---|---|---|---|---|---|
| 1 | i-PrMgCl 1a | 2a | 3a | 3-5 | 72 (80)[c] | 92[d] 94[e] 92[f] |
| 2 | i-PrMgCl 1a | 2b | 3b | 30 | 80 (93)[c] | 97[d] 98[e] |
| 3 | i-PrMgCl 1a | 2c | 3c | 30 | 73 | 95[d] 95[e] |
| 4 | i-PrMgCl 1a | 2d | 3d | 3 | — | 96[d] 95[e] 97[f] |
| 5 | 1b | 2d | 3e | 39 | 11 | 92[d] 91[e] |
| 6 | 1c | 2d | 3f | 37 | 8 | 86[d] 89[e] 88[f] |

TABLE 1-continued
Comparative reactions of ketones 2 with Grignard reagents 1 without additives and in the presence of CeCl$_3$ or MCl$_3$·2LiCl.
| Entry | Grignard reagent 1 | Ketone of type 2 | Product of type 3 | Without additives (%)[a] | CeCl$_3$ (%)[b] | MCl$_3$·2LiCl (%) |
|---|---|---|---|---|---|---|
| 7 | 1c 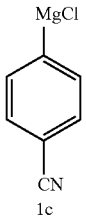 | 2c 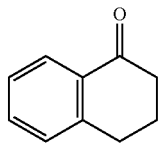 | 3g 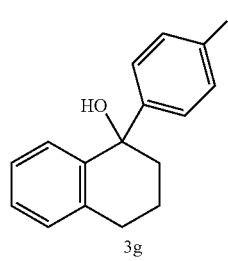 | 48 | 16 | 87[d] |
| 8 | 1c 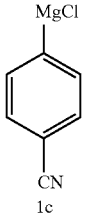 | 2e 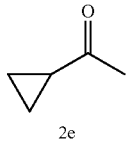 | 3h 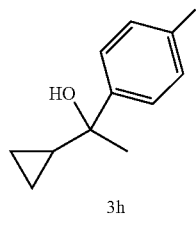 | 50 | — | 86[d] |
| 9 | 1c 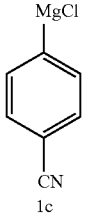 | 2a 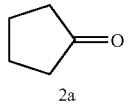 | 3i 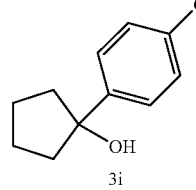 | 27 | — | 95[d]<br>94[e] |
| 10 | 1d 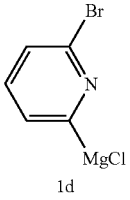 | 2f 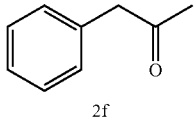 | 3j 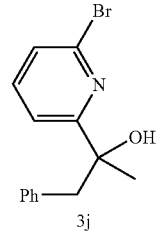 | 35 | — | 84[d] |
| 11 | 1e 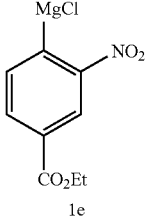 | 2g 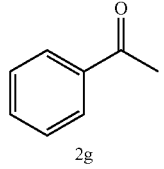 | 3k 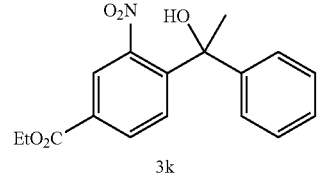 | 0 | 0 | 73[d] |
| 12 | MeMgCl 1f | 2h  | 3l 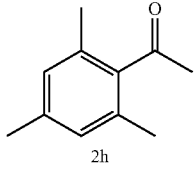 | 1 | 47 | 61[d]<br>65[e] |

TABLE 1-continued

Comparative reactions of ketones 2 with Grignard reagents 1 without additives and in the presence of CeCl₃ or MCl₃•2LiCl.

| Entry | Grignard reagent 1 | Ketone of type 2 | Product of type 3 | Without additives (%)[a] | CeCl₃ (%)[b] | MCl₃•2LiCl (%) |
|---|---|---|---|---|---|---|
| 13 | MgBr (1g) | 2i | 3l | 22 | 57 | 69[d] 71[e] |
| 14 | t-BuMgCl (1h) | 2b | 3m | 4 | — | 92[d] 93[e] |
| 15 | PhMgBr (1i) | 2j | 3n | 21 | — | 92[d] |
| 16 | 2-pyridyl-MgCl (1j) | 2j | 3o | 17 | 53 | 92[d] |

[a]Isolated Yield obtained by the direct reaction of the ketone with the Grignard reagent.
[b]Isolated yield obtained in the presence of CeCl₃ (1.5 equiv) according to the method of Imamoto.
[c]Isolated yield obtained in the presence of CeCl₃ (1.0 equiv) according to the method of Dimitrov.
[d]Reaction performed using LaCl₃•2LiCl (1.0 equiv).
[e]Reaction performed using CeCl₃•2LiCl (1.0 equiv).
[f]Reaction performed using NdCl₃•2LiCl (1.0 equiv).

Preparation of 1-isopropyl-cyclopentanol (3a)

According to Example 2, i-PrMgCl (3.30 mL; 3.30 mmol; 1.10 equiv) was reacted with cyclopentanone (252 mg; 3.00 mmol) in the presence of LaCl₃.2LiCl (0.33 M; 9.09 mL, 3.00 mmol, 1.00 equiv), the conversion was complete after 5 min (GC monitoring). After workup and careful evaporation of the solvents under reduced pressure, the desired product was obtained as colorless oil (353 mg, 92%). The analytical data were found to be in accordance with the literature data.
C. S. A. Antunes, M. Bietti, O. Lanzalunga, M. Salamome, *J. Org. Chem.* 2004, 16, 5281.

Preparation of 1-isopropyl-cyclohexanol (3b)

According to Example 2, i-PrMgCl (3.30 mL; 3.30 mmol; 1.10 equiv) was reacted with cyclohexanone (294 mg; 3.00 mmol) in the presence of LaCl₃.2LiCl (0.33 M; 9.09 mL, 3.00 mmol, 1.00 equiv), the conversion was complete after 5 min (GC monitoring). After workup and careful evaporation of the solvents under reduced pressure, the desired product was obtained as colorless oil (418 mg, 98%). The analytical data were found to be in accordance with the literature data.

C. S. A. Antunes, M. Bietti, O. Lanzalunga, M. Salamome, *J. Org. Chem.* 2004, 16, 5281.

Preparation of 1-isopropyl-1,2,3,4-tetrahydro-naphthalen-1-ol (3c)

According to Example 2, i-PrMgCl (1.10 mL; 1.10 mmol; 1.10 equiv) was reacted with 3,4-dihydro-1(2H)-naphthalenone (146 mg; 1.00 mmol) in the presence of LaCl₃.2LiCl (0.33 M; 3.00 mL, 1.00 mmol, 1.00 equiv), the conversion was complete after 5 min (GC monitoring). After workup and careful evaporation of the solvents under reduced pressure, the desired product was obtained as colorless oil (180 mg, 95%). The analytical data were found to be in accordance with the literature data.
T. Imamoto, Y. Sugiyura, N. Takiyama, T. Hatojima, Y. Kamiya, *J. Am. Chem. Soc.* 1989, 111, 4392.

Preparation of 2-benzyl-3-methyl-1-phenyl-butan-2-ol (3d)

According to Example 2, i-PrMgCl (1.10 mL; 1.10 mmol; 1.10 equiv) was reacted with 1,3-diphenylacetone (210 mg;

1.00 mmol) in the presence of LaCl$_3$.2LiCl (0.33 M; 3.0 mL, 1.00 mmol, 1.00 equiv), the conversion was complete after 5 min (GC monitoring). After workup and careful evaporation of the solvents under reduced pressure, the desired product was obtained as white solid, mp=52–53° C. (241 mg, 95%). The analytical data were found to be in accordance with the literature data.

G. Boche, K. Buckl, D. Martens, D. R. Schneider, *Liebigs Ann. Chem.* 1980, 7, 1135.

Preparation of 4-(1-benzyl-1-hydroxy-2-phenyl-ethyl)-benzoic acid ethyl ester (3e)

According to Example 2, the Grignard reagent 1b (freshly prepared via iodine-magnesium exchange[6] from ethyl-4-iodobenzoate (607 mg, 2.20 mmol, 1.10 equiv) and i-PrMgCl.LiCl (1.0 M in THF; 2.16 mL, 2.16 mmol, 1.08 equiv) at −20° C.) was reacted with diphenylacetone (420 mg; 2.00 mmol) in the presence of LaCl$_3$.2LiCl (0.33 M; 6.06 mL, 2.00 mmol, 1.00 equiv). The crude product was recrystallized from heptane to give 4-(1-benzyl-1-hydroxy-2-phenyl-ethyl)-benzoic acid ethyl ester (3e) as crystalline, colorless solid (662 mg, 92%).

mp: 126-128° C.
$^1$H-NMR (300 MHz, CDCl$_3$): δ [ppm]=7.94 (d, 2H, J=8.45 Hz); 7.34 (d, 2H, J=8.45 Hz); 7.15 (m, 6H); 6.95 (m, 4H); 4.37 (q, J=7.14 Hz); 3.32 (d, 2H, J=13.48 Hz); 3.13 (d, 2H, J=13.48 Hz); 1.99 (s, 1H); 1.39 (q, J=7.14 Hz).
$^{13}$C-NMR (300 MHz, CDCl$_3$): δ [ppm]=166.6; 150.5; 135.8; 130.6; 129.1; 128.7; 128.0; 126.7; 125.9; 77.2; 60.9; 48.7; 14.3.
MS (EI): m/z (%)=361 (0.4, [M+H]$^+$); 315 (5); 270 (19); 269 (100); 241 (3); 197 (6); 177 (22); 149 (6); 121 (3); 105 (10); 91 (14); 65 (3).
HR-MS: (C$_{24}$H$_{24}$O$_3$) calculated: 361.1804 ([M+H]$^+$). found: 361.1817.
IR (KBr): v/cm$^{-1}$=3500 (m); 3061 (w); 3030 (w); 2978 (w); 2920 (w); 1700 (vs); 1607 (s); 1571 (w); 1499 (m); 1477 (m); 1454 (m); 1405 (m); 1371 (s); 1316 (m); 1283 (vs); 1245 (s); 1204 (m); 1185 (m); 1160 (m); 1132 (s); 1113 (s); 1092 (s); 1066 (w); 1038 (m); 1020 (s); 992 (m); 919 (w); 902 (w); 884 (m); 851 (m); 777 (s); 754 (m); 722 (m), 700 (s); 698 (s); 664 (w).

Preparation of 4-(1-benzyl-1-hydroxy-2-phenyl-ethyl)-benzonitrile (3f)

According to Example 2, the Grignard reagent 1c (freshly prepared via bromine-magnesium exchange[6] from 4-bromo-benzonitrile (1.00 mmol) and i-PrMgCl.LiCl (1.05 mmol, 1.05 equiv) at −20° C.) was reacted with diphenylacetone (210 mg; 1.00 mmol) in the presence of LaCl$_3$.2LiCl (1.00 equiv). The crude product was recrystallized from heptane to give desired product as white solid, mp=153° C. (268 mg, 86%). The analytical data were found to be in accordance with the literature data.
K. Fukui et al. *J. Org. Chem.* 1972, 37, 3176.

Preparation of 4-(1-Hydroxy-cyclopentyl)-benzonitrile (3i)

According to Example 2, the Grignard reagent 1C (freshly prepared via bromine-magnesium exchange[6] from 4-bromo-benzonitrile (400 mg, 2.20 mmol, 1.10 equiv) and i-PrMgCl.LiCl (1.00 M in THF; 2.16 mL, 2.16 mmol, 1.08 equiv) at −20° C.) was reacted with cyclopentanone (168 mg; 2.00 mmol) in the presence of LaCl$_3$.2LiCl (0.33 M; 6.06 mL, 2.00 mmol, 1.00 equiv). The crude product was purified by flash column chromatography (silica; pentane:Et$_2$O, 7:3) to give the desired product as a colorless oil (355 mg, 95%).
$^1$H-NMR (300 MHz, CDCl$_3$): δ [ppm]=7.57 (s, 4H); 2.04 (s, 1H); 1.89 (m, 8H).
$^{13}$C-NMR (300 MHz, CDCl$_3$): δ [ppm]=152.3; 131.9; 125.8; 118.9; 110.2; 83.1; 42.4; 24.0.
MS (EI): m/z (%)=187 (27, M$^+$); 168 (9); 159 (12); 158 (100); 154 (6); 145 (41); 140 (9); 130 (55); 116 (7); 89 (4); 76 (4); 63 (2); 55 (7); 51 (3).
HR-MS: (C$_{12}$H$_{13}$NO) calculated: 187.0997. found: 187.0982.
IR (KBr): v/cm$^{-1}$=3436 (br); 2964 (s); 2874 (m); 2229 (vs); 1928 (w); 1725 (w); 1608 (s); 1503 (m); 1449 (w); 1402 (m); 1323 (w); 1183 (w); 1092 (w), 1040 (w); 1010 (s); 960 (w); 906 (w); 884 (w); 837 (s); 567 (s).

Preparation of 2-(6-bromo-pyridin-2-yl)-1-phenyl-propan-2-ol (3j)

According to Example 2, the Grignard reagent 1d (freshly prepared via bromine-magnesium exchange[6] from 2,5-dibromopyridine (391 mg, 1.65 mmol; 1.10 equiv) and i-PrMgCl.LiCl (1.00 M in THF; 1.62 mL, 1.62 mmol, 1.08 equiv) at −10° C.) was reacted with 1-phenyl-propan-2-one (201 mg; 1.50 mmol) in the presence of LaCl$_3$.2LiCl (0.33 M; 4.55 mL, 1.50 mmol, 1.00 equiv). The crude product was purified by flash column chromatography (silica; pentane:Et$_2$O, 9:1, 0.2 vol-% NEt$_3$) to give the desired product as colorless oil (355 mg, 81%).
$^1$H-NMR (300 MHz, CDCl$_3$): δ [ppm]=7.47 (t, 1H; J=7.75 Hz); 7.34 (d, 1H, J=7.81 Hz); 7.23 (d, 1H, J=7.81 Hz); 7.19 (m, 3H); 6.98 (m, 2H); 3.16 (d, 1H; J=13.54 Hz); 3.03 (d, 1H; J=13.54 Hz); 1.55 (s, 3H).
$^{13}$C-NMR (300 MHz, CDCl$_3$): δ [ppm]=166.7; 140.5; 138.8; 136.6; 130.4; 127.9; 126.5; 126.1; 118.4; 74.8; 49.5; 27.6.
MS (EI): m/z (%)=292 (0.1, M$^+$); 274 (2); 272 (2); 260 (1); 202 (95); 200 (100); 184 (15); 182 (14); 158 (6); 120 (4); 102 (12); 92 (39); 91 (39); 78 (25); 65 (13); 51 (5).
HR-MS: (C$_{14}$H$_{15}$BrNO) calculated: 292.0337. found: 292.0325.
IR (KBr): v/cm$^{-1}$=4062 (w); 3444 (br); 3085 (m); 3062 (m), 3028 (m); 2977 (m), 2922 (m); 2851 (w); 1950 (w); 1885 (w); 1808 (w); 1674 (w); 1581 (s); 1555 (s); 1496 (m); 1454 (s); 1430 (s); 1400 (s); 1366 (s); 1307 (s); 1232 (m); 1198 (m); 1159 (s); 1128 (s); 1080 (m); 1055 (m); 1031 (w); 987 (m); 951 (m); 909 (w); 872 (w); 797 (s); 781 (s); 739 (s); 702 (s); 676 (m); 659 (m); 643 (m); 624 (w); 566 (m); 465 (m).

Preparation of ethyl 4-(1-hydroxy-1-methyl-2-phenylethyl)-3-nitrobenzoate (3k)

According to Example 2, the Grignard reagent 1e (freshly prepared via iodine-magnesium exchange[6] from ethyl-4-iodo-3-nitrobenzoate (353 mg, 1.10 mmol; 1.10 equiv) and PhMgCl.LiCl (0.95 M in THF; 1.13 mL, 1.07 mmol, 1.07 equiv) at −50° C.) was reacted with 1-phenyl-propan-2-one (201 mg; 1.00 mmol) in the presence of LaCl$_3$.2LiCl (0.33 M; 3.03 mL, 1.00 mmol, 1.00 equiv). The crude product was purified by flash column chromatography (silica; pentane: Et$_2$O, 19:1) to give the desired product as yellow oil (231 mg, 73%).
$^1$H-NMR (300 MHz, CDCl$_3$): δ [ppm]=8.20 (m, 2H); 7.80 (d, J=8.13 Hz); 7.27 (m, 5H); 4.40 (q, 2H, J=7.11 Hz); 3.66 (s, 1H); 2.00 (s, 3H); 1.39 (t, 2H, J=7.11 Hz).

$^{13}$C-NMR (300 MHz, CDCl$_3$): δ [ppm]=164.1; 145.7; 144.4; 132.4; 131.1; 129.2; 128.4; 127.8; 126.0; 125.3; 112.6; 75.9; 61.9; 42.0; 31.0; 14.2.

MS (EI): m/z (%)=315 (0.4, M$^+$); 300 (100); 270 (5); 238 (5); 223 (6); 222 (46); 194 (3); 178 (2); 165 (2); 152 (5); 121 (9); 105 (3); 103 (2); 77 (4); 43 (7).

HR-MS: (C$_{17}$H$_{17}$NO$_5$) calculated: 315.1107. found: 315.1093.

IR (KBr): v/cm$^{-1}$=2982 (s); 1724 (vs); 1617 (m); 1542 (vs); 1494 (m); 1448 (m); 1370 (s); 1289 (vs); 1131 (s); 1019 (s); 912 (m); 861 (m); 837 (m); 767 (s); 735 (m); 701 (s); 671 (w).

Preparation of
2-(2,4,6-trimethyl-phenyl)-propan-2-ol (3l)

According to Entry 12, Table 1:

According to Example 2, MeMgCl (2.9 M; 0.76 mL, 2.2 mmol, 1.10 equiv) was reacted with 1-(2,4,6-trimethyl-phenyl)-ethanone (324 mg, 2.00 mmol) in the presence of LaCl$_3$.2LiCl (0.33 M; 6.06 mL, 2.00 mmol, 1.00 equiv). Column chromatographical purification (silica; pentane: Et$_2$O 9:1) afforded the desired product as colorless, crystalline solid, mp=106–107° C. (217 mg, 61%).

According to Entry 13, Table 1:

According to Example 3, mesitylmagnesium bromide (1.20 M in THF; 1.83 mL; 2.20 mmol; 1.10 equiv) was placed in a flame dried schlenk flask under an argon atmosphere and cooled to 0° C. At this temperature, LaCl$_3$.2LiCl (0.33 M; 6.06 mL, 2.00 mmol, 1.00 equiv) was slowly added. The resulting mixture was allowed to warm up to room temperature and stirred for 4 h. Then, after cooling to 0° C., acetone (116 mg; 2.00 mmol) was added and the reaction was warmed up to room temperature and stirred for another hour at this temperature. When the end of the reaction was reached (GC-monitoring of aliquots), sat. aq. NH$_4$Cl (2 mL) and water (2 mL) were added. The aqueous layer was extracted with ether (4×10 mL), the combined extracts were dried (Na$_2$SO$_4$) and evaporated in vacuo. Column chromatographical purification (silica; pentane:Et$_2$O 9:1) afforded the desired product as colorless, crystalline solid, mp=106–107° C. (245 mg, 69%).

In both cases, the analytical data were found to be in accordance with the literature data.

J. W. Timberlake, D. Pan, J. Murray, B. S. Jursic, T. Chen, *J. Org. Chem.* 1995, 16, 5295.

Preparation of 1-tert-butyl-cyclohexanol (3m)

According to Example 2, t-BuMgCl.LiCl (1.01 M in THF 2.18 mL; 2.20 mmol; 1.10 equiv) was reacted with cyclohexanone (178 mg; 2.00 mmol) in the presence of LaCl$_3$.2LiCl (0.33 M; 6.06 mL, 2.00 mmol, 1.00 equiv). Column chromatographical purification (silica; pentane:Et$_2$O, 9:1) afforded the desired product as colorless oil, which started to crystallize after being chilled, mp=49–50° C. (287 mg, 92%).

The analytical data were found to be in accordance with the literature data.

C. S. A. Antunes, M. Bietti, O. Lanzalunga, M. Salamome, *J. Org. Chem.* 2004, 16, 5281.

Preparation of
1,7,7-trimethyl-2-phenyl-bicyclo[2.2.1]heptan-2-ol
(3n)

According to Example 2, PhMgBr.LiCl (1.00 M in THF; 1.10 mL; 1.10 mmol; 1.10 equiv) was reacted with 1,7,7-trimethylbicyclo[2.2.1]heptan-2-one (152 mg; 1.00 mmol) in the presence of LaCl$_3$.2LiCl (0.33 M; 3.03 mL, 1.00 mmol, 1.00 equiv). Column chromatographical purification (silica; pentane:Et$_2$O, 9:1) afforded the desired product as white solid, mp=41–42° C. (211 mg, 92%).

The analytical data were found to be in accordance with the literature data.

G. Rueedi, H.-J. Hansen, *Helv. Chim. Acta,* 2004, 87, 1968.

Preparation of 1,7,7-trimethyl-2-pyridin-2-yl-bicyclo
[2.2.1]-heptan-2-ol (3o)

According to Example 2, 2-PyMgCl.LiCl (1.00 M in THF; 1.10 mL; 1.10 mmol; 1.10 equiv) was reacted with 1,7,7-trimethylbicyclo[2.2.1]heptan-2-one (152 mg; 1.00 mmol) in the presence of LaCl$_3$.2LiCl (0.33 M; 3.03 mL, 1.00 mmol, 1.00 equiv) at –20° C. Column chromatographical purification (silica; pentane:CH$_2$Cl$_2$, 5:1) afforded the desired product as white solid, mp=60–61° C. (212 mg, 92%). The analytical data were found to be in accordance with the literature data.

W. A. Herrmann, J. J. Haider, J. Fridgen, G. M. Lobmaier, M. Spiegler, *J. Organomet. Chem.* 2000, 503, 69.

Preparation of 1-cyclopentyl-cyclohex-2-enol (6)

According to Example 2, cyclopentylmagnesium bromide (1.00 M in THF, 2.10 mL; 2.10 mmol; 1.05 equiv) was reacted with cyclohexenone (192 mg; 2.00 mmol) in the presence of LaCl$_3$.2LiCl (0.33 M; 6.06 mL, 2.00 mmol, 1.00 equiv). Gel filtration (silica; pentane:Et$_2$O 9:1, 0.5 vol-% NEt$_3$) afforded 1-Cyclopentyl-cyclohex-2-enol (7) as colorless oil (306 mg, 93%).

$^1$H-NMR (300 MHz, CDCl$_3$): δ [ppm]=5.82 (m, 1H); 5.65 (brd, 1H; J=10.15 Hz).

$^{13}$C-NMR (300 MHz, CDCl$_3$): δ [ppm]=131.6; 130.4; 112.6; 71.0; 49.7; 41.7; 34.6; 26.9; 26.5; 26.0; 25.4; 18.7.

MS (EI): m/z (%)=166 (0.1; M$^+$); 149 (4); 138 (3); 97 (100); 79 (5); 77 (2); 69 (5); 67 (4).

HR-MS: (C$_{11}$H$_{18}$O) calculated: 166.1358. found: 166.1363.

IR (KBr): v/cm$^{-1}$=3430 (br); 3023 (m); 2948 (vs); 2867 (s); 2833 (m); 1647 (w); 1452 (m); 1438 (m); 1402 (w); 1321 (w); 1172 (m); 1099 (w); 1063 (m); 981 (m); 966 (m); 930 (m); 884 (w); 851 (w); 734 (m); 533 (w).

Attempted Preparation of
1-cyclopentyl-cyclohex-2-enol (6); and Isolation of
cyclohex-2-enol (7)

Cyclopentylmagnesium bromide (1.00 M in THF, 2.10 mL; 2.10 mmol; 1.05 equiv) was added to a solution of cyclohexenone (192 mg; 2.00 mmol) in absolute THF at 0° C. After 15 min, GC and GC/MS monitoring indicated complete conversion to the reduction product, cyclohexenol (7). Then, sat. aq. NH$_4$Cl (2 mL) and water (2 mL) was added and the aqueous layer was extracted with ether (4×10 mL). The combined extracts were dried (Na$_2$SO$_4$) and carefully evaporated under reduced pressure. Gel filtration (silica; pentane:Et$_2$O, 9:1) afforded cyclohex-2-enol (7) as colorless oil (151 mg, 77%).

P. Saravanan, A. DattaGupta, D. Bhuniya, V. K. Singh, *Tetrahedron* 1997, 53, 1855.

Preparation of 1-butyl-cyclopentanol (8)

nBuLi (1.00 mL; 1.50 mmol; 1.00 equiv) was added to a solution of cyclopentenone (84 mg; 1.0 mmol) in the presence of LaCl$_3$.2LiCl (0.33 M; 3.03 mL, 1.00 mmol, 1.00 equiv) at 0° C. After 2 min, sat. aq. NH$_4$Cl (2 mL) and water (2 mL) was added and the aqueous layer was extracted with ether (4×10 mL). The combined extracts were dried (Na$_2$SO$_4$). Careful evaporation under reduced pressure afforded analytically clean 1-butylcyclopentanol (8) as colorless oil (139 mg, 98%). The analytical data were found to be in accordance with the literature data.

C. Walling, A. Padwa, *J. Am. Chem. Soc.* 1963, 85, 1597.

Preparation of (4-methoxy-phenyl)-(2-methyl-1-phenyl-propyl)-amine (9)

According to Example 2, i-PrMgCl.LiCl (1.00 M in THF, 1.10 mL; 1.10 mmol; 1.10 equiv) was reacted with 4-methoxy-N-[(E)-phenylmethylidene]aniline (9) (212 mg; 1.00 mmol) in the presence of LaCl$_3$.2LiCl (0.33 M; 0.30 mL, 0.10 mmol, 0.10 equiv) at room temperature for 12 h. Column chromatographical purification afforded the desired product 10 as colorless oil (214 mg, 84%). The analytical data were found to be in accordance with the literature data.

S. Saito, K. Hatanaka, H. Yamamoto, *Syn. Lett.* 2001, 12, 1859.

Preparation of allyl-(1-pyridin-3-yl-allyl)-amine (12)

According to Example 2, vinyl magnesium chloride (1.00 M in THF, 1.10 mL; 1.10 mmol; 1.10 equiv) was reacted with N-[(E)-3-pyridinylmethylidene]-2-propen-1-amine (11) (146 mg; 1.00 mmol) in the presence of LaCl$_3$.2LiCl (0.33 M; 0.30 mL, 0.10 mmol, 0.10 equiv) at room temperature for 1 h. Column chromatographical purification afforded the desired product 12 as colorless oil (151 mg, 87%). The analytical data were found to be in accordance with the literature data.

C. Agami, F. Couty, G. Evano, *Tetrahedron: Asymmetry* 2000, 11, 4639-4644.

Even though the present invention was described in detail above using specific examples of e.g. lanthanides and concentrations, it will be obvious to a person skilled in the art that the present invention can be modified in many ways and is applicable in a wide field of reactions. The solution of lanthanide halides according to the invention can be used in any reaction wherein lanthanides are known to have an effect. Such reactions may include reduction reactions, Diels-Alder reactions or other reactions using Lewis acids.

REFERENCES

[1] a) S. Kobayashi, M. Sugiura, H. W. L. Lam, *Chem. Rev.* 2002, 102, 2227; b) S. Kobayashi, K. Manabe, *Acc. Chem. Res.* 2002, 35, 209.

[2] a) T. Imamoto, Y. Sugiyura, N. Takiyama, *Tetrahedron Lett.* 1984, 25, 4233; b) T. Imamoto, N. Takiyama, K. Nakamura, *Tetrahedron Lett.* 1985, 26, 4763; c) T. Imamoto, Y. Sugiyura, N. Takiyama, T. Hatojima, Y. Kamiya, *J. Am. Chem. Soc.* 1989, 111, 4392; c) H. Schumann, M. Glanz, J. Gottfriedsen, S. Dechert, D. Wolff, *Pure and Appl. Chem.* 2001, 73, 279; d) J.-L. Luche, *J. Am. Chem. Soc.* 1978, 100, 2226; e) A. L. Gemal, J.-L. Luche, *J. Am. Chem. Soc.* 1981, 103, 5454

[3] V. Dimitrov, K. Koslova, M. Genov, *Tetrahedron Lett.* 1996, 37, 6787.

[4] a) U. Groth, M. Jeske, *Angew. Chem. Int. Ed.* 2000, 39, 574; b) U. Groth, M. Jeske, *Synlett* 2001, 129; c) S. Fischer, U. Groth, M. Jeske, T. Schutz, *Synlett* 2002, 1922; see also d) W.-D. Z. Li, J.-H. Yang, *Org. Lett.* 2004, 6, 1849; e) D. Tsvelikhovsky, D. Gelman, G. A. Molander, J. Blum, *Org. Lett.* 2004, 6, 1995; f) M. Shenglof, D. Gelman, G. A. Molander, J. Blum, *Tetrahedron Lett.* 2003, 44, 8593; g) P. Eckenberg, U. Groth, T. Köhler, *Liebigs Ann. Chem.* 1994, 673; h) M. Hatano, T. Matsuma, K. Ishkihara, *Org. Lett.* 2005, 7, 573; i) S. Fukuzawa, T. Fujinami, S. Yamauchi, S. Sakai, *J. Chem. Soc. Perkin Trans. I* 1986, 1929; j) F. T. Edelmann, D. M. M. Freckmann, H. Schumann, *Chem. Rev.* 2002, 102, 1851.

[5] Y. Y. Novikov, P. Sampson, *Org. Lett.* 2003, 3, 2263.

[6] A. Krasovskiy, P. Knochel, *Angew. Chem. Int. Ed.* 2004, 43, 3333.

The invention claimed is:

1. Anhydrous solution of MX$_3$.zLiA in a solvent, wherein
    M is selected from the group consisting of yttrium, indium and the lanthanides including lanthanum;
    z is greater than 0.5 and less than 3; and
    X and A are both independently monovalent anions selected from the group consisting of F; Cl; Br; I; CN; SCN; NCO; HalO$_n$, wherein n=3 or 4 and Hal is selected from Cl, Br and I; NO$_3$; BF$_4$; PF$_6$; AsF$_6$; SbF$_6$; H; a carboxylate of the general formula RCO$_2$; a disilazide of the general formula (R$_3$Si)$_2$N; a thiolate of the general formula SR; RP(O)O$_2$; SCOR; an amine of the general formula RNH; a dialkyl or diarylamine of the general formula R$_2$N, wherein R is defined as below or R$_2$N represents a cyclic alkylamine; a phosphine of the general formula PR$_2$, wherein R is defined as below or PR$_2$ represents a cyclic phosphine; O$_n$SR, wherein n=2 or 3; and NO$_n$, wherein n=2 or 3;
    wherein R is selected from the group consisting of a substituted or unsubstituted C$_4$-C$_{24}$ aryl or a C$_3$-C$_{24}$ heteroaryl containing one or more heteroatoms selected from B, O, N, S, Se, P, or Si; a linear or branched unsubstituted C$_1$-C$_{20}$ alkyl; a C$_2$-C$_{20}$ alkenyl or a C$_2$-C$_{20}$ alkynyl; a substituted or unsubstituted C$_3$-C$_{20}$ cycloalkyl; and H.

2. Solution according to claim 1, wherein X and A are both independently Cl, Br or I.

3. Solution according to claim 1, wherein M is selected from the group consisting of lanthanum, cerium, neodymium, and praseodymium.

4. Solution according to claim 1, wherein z is greater or equal to 2 and less than 3.

5. Solution according to claim 1, wherein the solvent is a solvent suitable for dissolving salts.

6. Solution according to claim 5, wherein the solvent is selected from the group consisting of cyclic, linear or branched monoethers or polyethers, thioethers, amines, phosphines, and derivatives thereof containing one or more additional heteroatoms selected from O, N, S and P; cyclic amides; cyclic, linear or branched alkanes and/or alkenes wherein one or more hydrogens are replaced by a halogen; solvents containing an urea group; aromatic, heteroaromatic or aliphatic hydrocarbons; hexamethylphosphorus triamide (HMPA), CS$_2$; and combinations thereof.

7. Solution according to claim 6, wherein the solvent is selected from the group consisting of tetrahydrofuran (THF), 2-methyltetrahydrofuran, dibutyl ether, diethyl ether, tert-butylmethyl ether, dimethoxyethane, dioxanes, 1,4-dioxane, triethylamine, ethyldiisopropylamine, dimethylsulfide, dibutylsulfide, N-methyl-2-pyrrolidone (NMP), N-ethyl-2-pyrrolidone (NEP), N-butyl-2-pyrrolidone (NBP), dichloromethane, 1,2-dichloroethane, CCl$_4$, N,N'-dimethylpropyleneurea (DMPU), benzene, toluene, xylene, pyridine, pentane, cyclohexane, hexane, heptane, and combinations thereof.

8. Solution according to claim 1, wherein said M is contained in the solution in a concentration of up to 3 mol/l.

9. Solution according to claim 1, wherein the solution is stored with the addition of a drying agent.

10. Solution according to claim 9, wherein the drying agent is selected from the group consisting of a molecular sieve, sodium hydride, calcium hydride, silica perls, silica powder, aluminium oxide, sodium sulfate, magnesium sulfate and sodium phosphate.

11. A salt of the formula $MX_3 \cdot zLiA$, wherein
   M is selected from the group consisting of yttrium, indium and the lanthanides including lanthanum;
   z is greater than 0.5 and less than 3; and
   X and A are both independently monovalent anions selected from the group consisting of F; Cl; Br; I; CN; SCN; NCO; $HalO_n$, wherein n=3 or 4 and Hal is selected from Cl, Br and I; $NO_3$; $BF_4$; $PF_6$; $AsF_6$; $SbF_6$; H; a carboxylate of the general formula $RCO_2$; a disilazide of the general formula $(R_3Si)_2N$; a thiolate of the general formula SR; $RP(O)O_2$; SCOR; an amine of the general formula RNH; a dialkyl or diarylamine of the general formula $R_2N$, wherein R is defined as below or $R_2N$ represents a cyclic alkylamine; a phosphine of the general formula $PR_2$, wherein R is defined as below or $PR_2$ represents a cyclic phosphine; $O_nSR$, wherein n=2 or 3; and $NO_n$, wherein n=2 or 3;
   wherein R is selected from the group consisting of a substituted or unsubstituted $C_4$-$C_{24}$ aryl or a $C_3$-$C_{24}$ heteroaryl containing one or more heteroatoms selected from B, O, N, S, Se, P, or Si; a linear or branched unsubstituted $C_1$-$C_{20}$ alkyl; a $C_2$-$C_{20}$ alkenyl or a $C_2$-$C_{20}$ alkynyl; a substituted or unsubstituted $C_3$-$C_{20}$ cycloalkyl; and H.

12. A salt according to claim 11, wherein $MX_3 \cdot zLiA$ is in the form of an adduct with a solvent.

13. A salt according to claim 12, wherein each M holds 1 to 6 solvent molecules.

14. A salt according to claim 13, wherein each M holds 2 to 3 solvent molecules.

15. A salt according to claim 12, wherein the solvent is selected from the group consisting of cyclic, linear or branched monoethers or polyethers, thioethers, amines, phosphines, and derivatives thereof containing one or more additional heteroatoms selected from O, N, S and P; cyclic amides; cyclic, linear or branched alkanes and/or alkenes wherein one or more hydrogens are replaced by a halogen; solvents containing an urea group; aromatic, heteroaromatic or aliphatic hydrocarbons; hexamethylphosphorus triamide (HMPA), $CS_2$; and combinations thereof.

16. A salt according to claim 15, wherein the solvent is selected from the group consisting of tetrahydrofuran (THF), 2-methyltetrahydrofuran, dibutyl ether, diethyl ether, tert-butylmethyl ether, dimethoxyethane, dioxanes, 1,4-dioxane, triethylamine, ethyldiisopropylamine, dimethylsulfide, dibutylsulfide, N-methyl-2-pyrrolidone (NMP), N-ethyl-2-pyrrolidone (NEP), N-butyl-2-pyrrolidone (NBP), dichloromethane, 1,2-dichloroethane, $CCl_4$, N,N'-dimethylpropyleneurea (DMPU), benzene, toluene, xylene, pyridine, pentane, cyclohexane, hexane, heptane, and combinations thereof.

17. A salt according to claim 11, wherein z is greater or equal to 2 and less than 3.

18. A method of conducting a chemical reaction, wherein the method comprises conducting a chemical reaction in contact with a solution of claim 1.

19. A method according to claim 18, wherein the chemical reaction is an addition reaction of a nucleophile to a compound comprising a carbonyl group or a carboxylic acid group.

20. Method for the preparation of an anhydrous solution of $MX_3 \cdot zLiA$ in a solvent according to claim 1, comprising:
   a) Close mixing of $MX_3$ and z equivalents of LiA, optionally in a first solvent;
   b) Removing any solvent or water or a combination thereof from the mixture formed in step a); and
   c) Adding a second solvent to the powder formed in step b) to form a solution.

21. Method according to claim 20, wherein $MX_3$ is in the form of a hydrate or an adduct with solvent.

22. Method according to claim 20, wherein the first solvent is selected from water, a hydrophilic solvent or a mixture thereof.

23. Method according to claim 20, wherein at least one step is carried out under stirring.

24. Method according to claim 20, wherein said removing of any solvent or water or a combination thereof in step b) is carried out under reduced pressure.

25. Method according to claim 20, wherein said removing of any solvent or water or a combination thereof is carried out while heating.

26. Method according to claim 25, wherein the temperature is in the range of 20-220° C. while heating.

27. Method according to claim 25 or 26, wherein the temperature is raised stepwise or continuously while heating.

28. Method according to claim 20, wherein the second solvent is selected from the group consisting of cyclic, linear or branched monoethers or polyethers, thioethers, amines, phosphines, and derivatives thereof containing one or more additional heteroatoms selected from O, N, S and P; cyclic amides; cyclic, linear or branched alkanes and/or alkenes wherein one or more hydrogens are replaced by a halogen; solvents containing an urea group; aromatic, heteroaromatic or aliphatic hydrocarbons; hexamethylphosphorus triamide (HMPA), $CS_2$; and combinations thereof.

29. Method according to claim 28, wherein the solvent is selected from the group consisting of tetrahydrofuran (THF), 2-methyltetrahydrofuran, dibutyl ether, diethyl ether, tert-butylmethyl ether, dimethoxyethane, dioxanes, 1,4-dioxane, triethylamine, ethyldiisopropylamine, dimethylsulfide, dibutylsulfide, N-methyl-2-pyrrolidone (NMP), N-ethyl-2-pyrrolidone (NEP), N-butyl-2-pyrrolidone (NBP), dichloromethane, 1,2-dichloroethane, $CCl_4$, N,N'-dimethylpropyleneurea (DMPU), benzene, toluene, xylene, pyridine, pentane, cyclohexane, hexane, heptane, and combinations thereof.

30. Method according to claim 20, wherein at least one step is carried out under an inert gas atmosphere.

* * * * *